(12) United States Patent
Choung et al.

(10) Patent No.: US 8,775,100 B2
(45) Date of Patent: Jul. 8, 2014

(54) CABLE FOR INSPECTING HEAT TUBES AND METHOD OF ANALYZING INSERTION FORCE OF CABLE

(75) Inventors: Yun Hang Choung, Daejeon (KR); Dong Ok Kim, Daejeon (KR); Jin Seok Park, Daejeon (KR); Won Jae Lee, Chungcheongnam-do (KR); Hark Rho Kim, Daejeon (KR); Hyun Kyu Jung, Daejeon (KR); Yong Chil Seo, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 535 days.

(21) Appl. No.: 13/016,878

(22) Filed: Jan. 28, 2011

(65) Prior Publication Data

US 2012/0053857 A1 Mar. 1, 2012

(30) Foreign Application Priority Data

Aug. 30, 2010 (KR) .................. 10-2010-0083829

(51) Int. Cl.
*G01B 5/30* (2006.01)
*G01M 5/00* (2006.01)

(52) U.S. Cl.
CPC ..... *G01M 5/0033* (2013.01); *G01N 2291/0258* (2013.01)
USPC .......................................... 702/35

(58) Field of Classification Search
CPC .................. G01N 2291/0258; G01M 5/0033
USPC .................................... 702/41, 35
See application file for complete search history.

(56) References Cited

U.S. PATENT DOCUMENTS

| | | | |
|---|---|---|---|
| 3,930,487 A * | 1/1976 | Gugel | 226/91 |
| 4,515,747 A * | 5/1985 | Creek et al. | 376/249 |
| 5,174,164 A | 12/1992 | Wilheim | |
| 5,174,165 A | 12/1992 | Pirl | |
| 6,450,104 B1 | 9/2002 | Grant | |
| 7,055,656 B2 * | 6/2006 | Drew | 188/65.1 |
| 2012/0006134 A1 * | 1/2012 | Draper et al. | 73/866.5 |

FOREIGN PATENT DOCUMENTS

| | | |
|---|---|---|
| EP | 104492 A2 | 4/1984 |
| FR | 2211622 A1 | 11/1973 |
| JP | 05-256984 H | 10/1993 |
| JP | 2002-318293 A | 10/2002 |
| WO | 0206720 A1 | 1/2002 |
| WO | 02070943 A2 | 9/2002 |

OTHER PUBLICATIONS

European Search Report; Application No. EP 10 19 4471; Aug. 11, 2011; Korea Atomic Energy Research Institute; Reference KORA.210.01 EP.
JP_2002-318293 English translation by machine (D2_JPA2002-318293_english).
JP Office Action (Japanese_OA_FPM-10-0176JP_OA), Aug. 16, 2012.

* cited by examiner

*Primary Examiner* — Michael Nghiem
(74) *Attorney, Agent, or Firm* — Saliwanchik, Lloyd & Eisenschenk

(57) ABSTRACT

A heat tube inspection cable and a method of analyzing an insertion force of the cable are disclosed. The heat tube inspection cable includes a sensor unit configured to detect a defect in a heat tube, a plurality of segment units each configured to comprise a body part and a wheel part rotatably connected to the body part, a signal cable configured to helically pass through the body part of each of the plurality of segment units to transmit electric signal from the sensor unit, and a wire configured to pass through the body part of each of the plurality of segment units to keep the linear configuration of the plurality of segment units like a bead necklace and to provide axial and bending strength.

16 Claims, 9 Drawing Sheets

# CABLE FOR INSPECTING HEAT TUBES AND METHOD OF ANALYZING INSERTION FORCE OF CABLE

CROSS-REFERENCE TO RELATED APPLICATION

This application claims the benefit of Korean Patent Application No. 10-2010-0083829, filed on Aug. 30, 2010, in the Korean Intellectual Property Office, the disclosure of which is incorporated herein by reference.

BACKGROUND

1. Field of the Invention

The present invention relates to a cable of a defect detection sensor for inspecting heat tubes and a method of analyzing an insertion force of the cable, and more particularly, to an inspection cable enabling inspection of a defect in a slender heat tube by reducing frictional resistance generated when inserting a defect detection sensor into a tube of a helical heat exchanger, and a method of analyzing an insertion force required to insert the tube defect detection sensor into the tube of the helical heat exchanger.

2. Description of the Related Art

In general, a nuclear power plant produces electricity by supplying steam generated by a steam generator to a turbine. The steam generator performs heat exchange between a high-temperature high-pressure primary coolant flowing in a heat tube of a heat exchanger and a secondary coolant flowing outside of the heat tube. As a result of the heat exchange, the secondary coolant turns to steam.

The primary coolant circulating inside the steam generator is high-temperature high-pressure water. The primary coolant is contaminated by radioactive substances while heated and flowing through the nuclear reactor. Therefore, if the heat tube is broken, the primary coolant may contaminate the secondary coolant, causing leakage of radioactivity.

Since the heat tube of the steam generator forms a barrier between the primary coolant which is radioactive and the secondary coolant which is non-radioactive, an integrity inspection of the heat tube is strictly regulated by rules and standards with the regular in-service inspection (ISI) and schedule.

Generally, during an inspection for a heat tube of a steam generator of a commercial nuclear power plant and an inspection for a heat tube of a general heat exchanger, an eddy current test (ECT) probe is inserted in the heat tube to inspect whether the heat tube has a defect, accordingly determining soundness of the heat tube. For the inspection, an ECT sensor unit consisting of the ECT probe and a cable is necessary, which is appropriate for a size and a shape of the heat tube of the steam generator.

The cable is composed of signal cables and a protection cable. The ECT probe is connected at a leading end of the cable.

When the heat tube of the steam generator is a straight tube or has a few curved parts, friction resistance between the cable and the heat tube is low and, therefore, the ECT sensor unit is readily inserted into the heat tube.

An integrated nuclear reactor recently developed has the steam generator units inside its reactor vessel, and the steam generators are equipped with once-through type helical heat tubes.

Generally, a force to insert a defect detection sensor for inspecting the heat tube of the commercial nuclear power plant is proportional to the inserted length of the cable with sensor.

However, since the heat tube of the integrated nuclear reactor is a helical shape, the insertion force of the defect detection sensor exponentially increases, thereby causing a difficulty in inserting the defect detection sensor with a conventional inspection cable.

Accordingly, there is a desire for a method to analyze the insertion force of the cable in the helical heat tube so as to improve easiness of inserting the ECT probe into the helical heat tube.

SUMMARY

An aspect of the present invention provides a heat tube inspection cable capable of being inserted in a long helical heat tube of a steam generator by minimizing frictional resistance of the cable.

Another aspect of the present invention provides a method for analyzing an insertion force of the heat tube inspection cable capable of analyzing factors that influence the insertion force of the heat tube inspection cable to be inserted in a long curved heat tube.

According to an aspect of the present invention, there is provided a heat tube inspection cable including a sensor unit configured to detect a defect in a heat tube, a plurality of segment units each configured to include a body part and a wheel part rotatably connected to the body part, signal cables configured to helically pass through the body part of each of the plurality of segment units to transmit electronic signal from the sensor unit, and a steel wire configured to pass through the body part of each of the plurality of segment units to keep the linear configuration of the plurality of segment units like a bead necklace and to provide axial and bending strength.

According to another aspect of the present invention, there is provided a heat tube inspection cable including a sensor unit configured to detect a defect in a heat tube, a plurality of segment units each configured to include a body part and wheel parts, one side of a wheel part protruding out of the body part and the other side extending to be proximate to an inner center of the body, signal cables configured to helically pass between the wheel parts of each of the segment units, and to extend in a length direction of the body part and a wire configured to pass through the body part of each of the segment units to keep the linear configuration of the plurality of segment units like a bead necklace and to provide axial and bending strength.

According to another aspect of the present invention, there is provided a heat tube inspection cable including a sensor unit configured to detect in a heat tube, a plurality of segment units each configured to include a body part and a single wheel part passing through the body part, signal cables configured to helically pass at both sides of the single wheel part of each of the segment units, and to extend in a length direction of the body part, and steel wires configured to helically pass through the body part of each of the segment units to keep the linear configuration of the plurality of segment units like a bead necklace and to provide axial and bending strength, wherein both ends of each wheel part protrude out of each body part.

According to another aspect of the present invention, there is provided a method of analyzing an insertion force of a heat tube inspection cable including a sensor unit to detect a defect of the heat tube, and a cable of which an end is connected with the sensor unit, wherein determining an insertion force to insert the cable is based on a contact force B of the cable against the inner circumference of the heat tube, a curvature radius R of the heat tube, a frictional coefficient μ between the heat tube and the cable, an insertion length L by which the cable is inserted in the heat tube, and a minimum force, $S_{tip}$, used to insert the sensor unit into the heat tube, and the insertion force is calculated by the following equation:

$$S_O(L) = (S_{tip} + BR)e^{-\frac{\mu}{R}L} - BR.$$

Effect

According to embodiments of the present invention, since friction between a heat tube and a heat tube inspection cable is reduced, the heat tube inspection cable is inserted in the heat tube with a small force.

According to embodiments of the present invention, a steam generator may be designed in various manners since the heat tube inspection cable is not strictly determined by a shape and size of the heat tube inspection cable.

Additionally, according to embodiments of the present invention, vibration caused by friction generated during insertion and withdrawal of the cable may reduce, thereby reducing noise signal that affect the quality of the signal from the sensor.

Additionally, according to embodiments of the present invention, the defect detection may be achieved with a relatively simple equipments without requiring accessories such as a pneumatic push puller and the like, which may be used for detecting a defect in the helical heat tubes. Accordingly, cost, time, an installation space, and the like may be reduced.

Additionally, according to embodiments of the present invention, since the inspection may be performed individually to a single heat tube of each steam generator, the overall lifespan of the steam generator may be increased by finding and repairing or plugging degraded heat tubes.

Additionally, according to embodiments of the present invention, the heat tube inspection cable is directly applicable to an existing an eddy current test (ECT) device. Therefore, the heat tube inspection cable is ready to commercial application. Also, the infrastructure for development of the product is already prepared.

Additionally, according to embodiments of the present invention, an insertion force and a withdrawal force of the heat tube inspection cable may be analyzed mathematically.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention by referring to the accompanying drawings. However, the aspect of the invention is not limited to the embodiments but components of the embodiments may be added, modified, or deleted without departing the scope of the invention.

Figure 1:
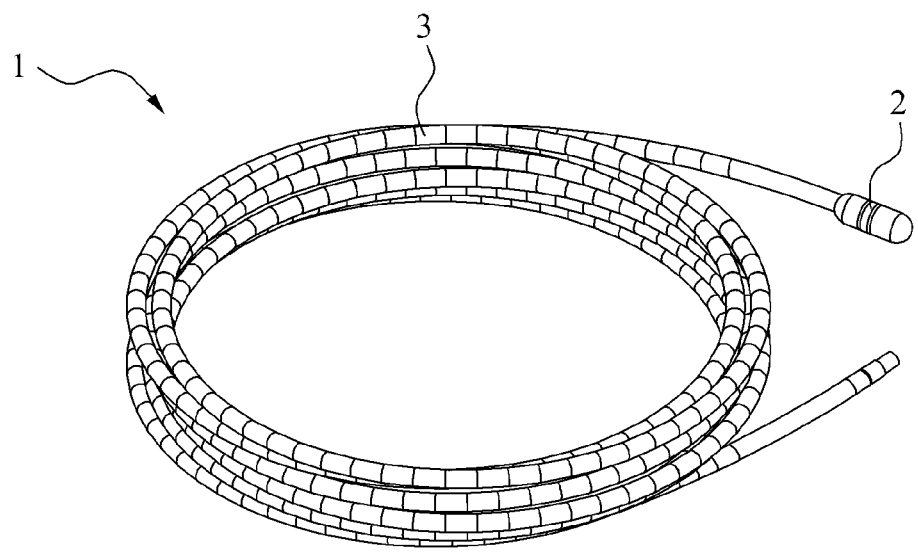
FIG. 1 is a perspective diagram illustrating a heat tube inspection cable according to an embodiment of the present invention.
Figure 2:
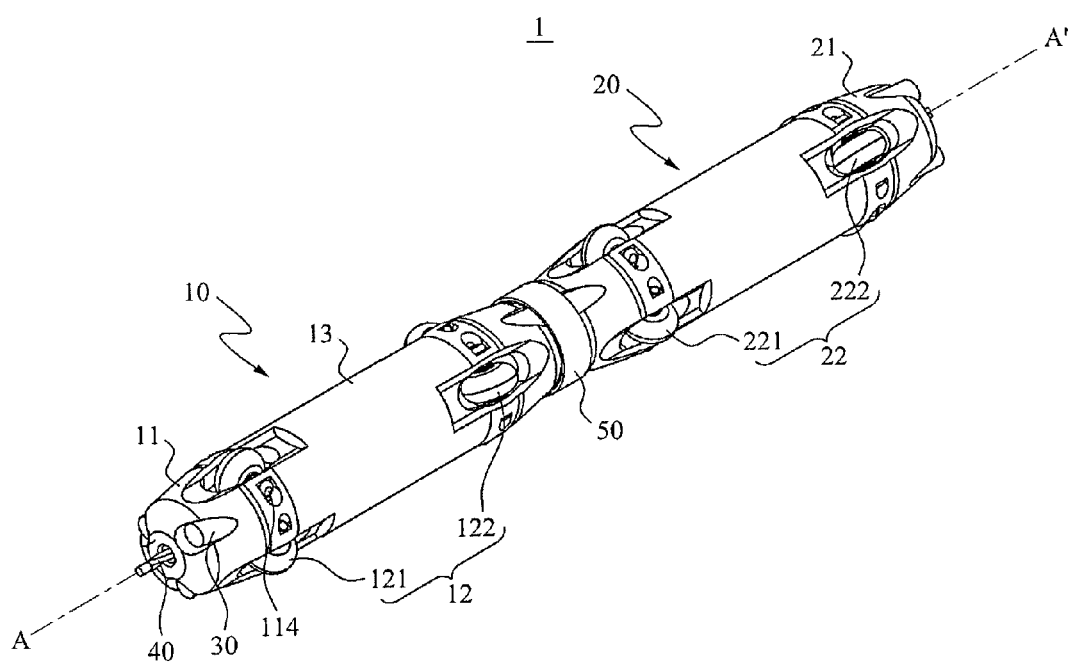
FIG. 2 is a perspective diagram illustrating two segment units of the heat tube inspection cable of FIG. 1.
Figure 3:
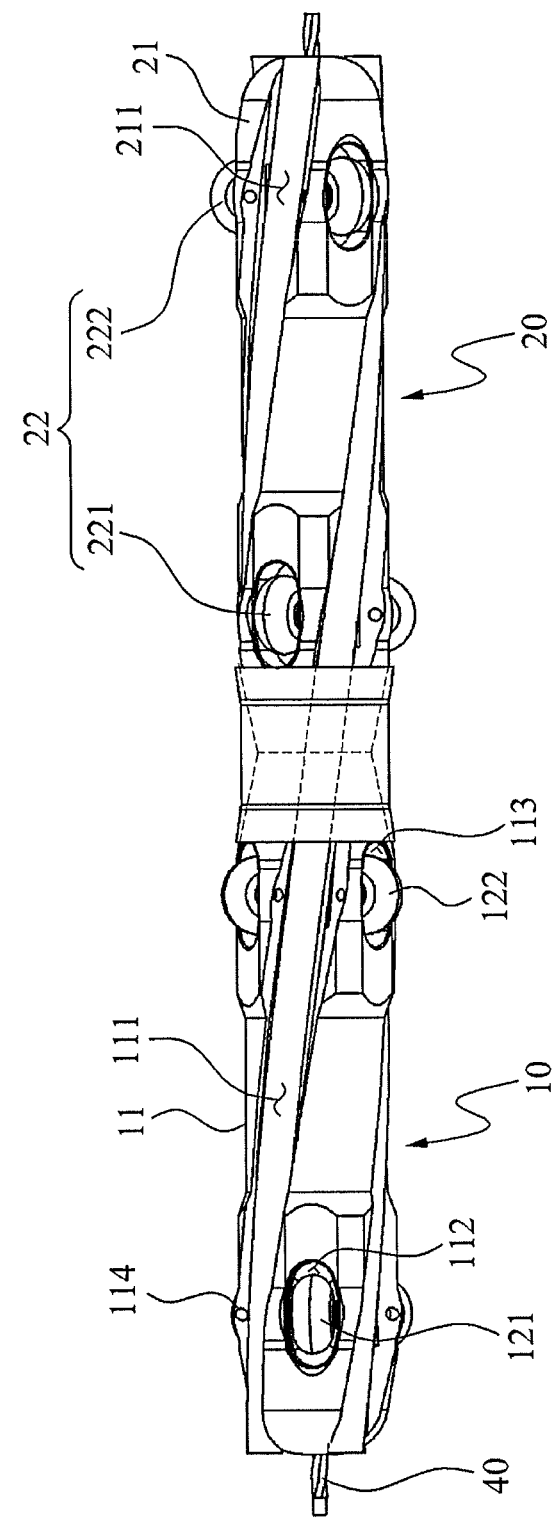
FIG. 3 is a perspective diagram illustrating insides of the segment units of FIG. 2.
Figure 4A:
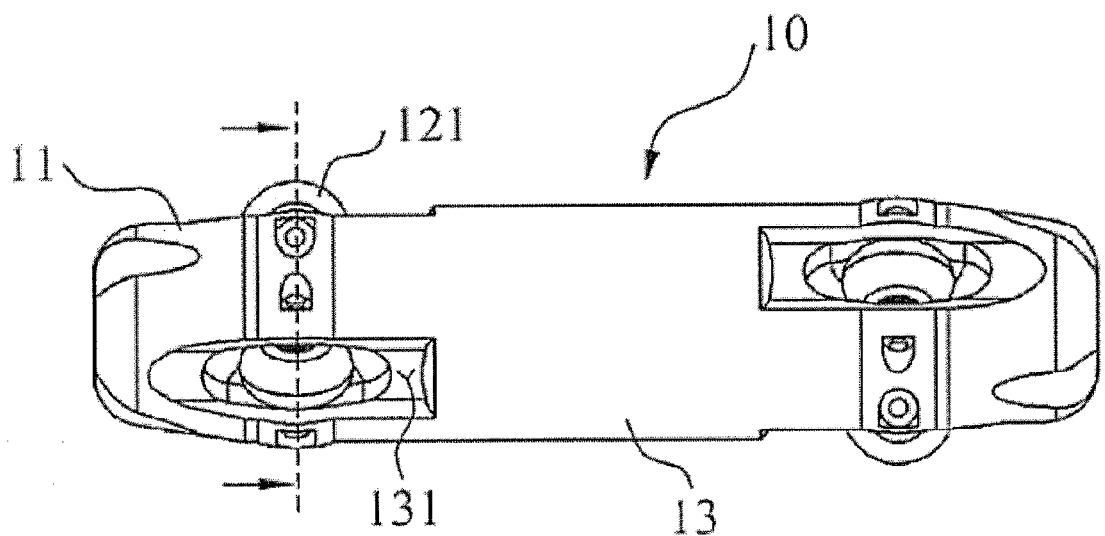
FIGS. 4A and 4B are for sectional diagram of the segment unit of FIG. 2.
Figure 4B:
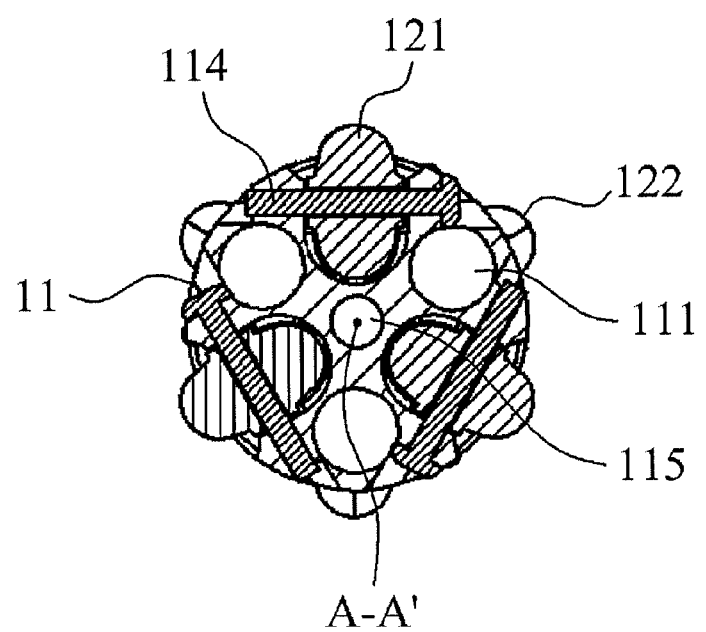

FIG. 1 is a perspective diagram of a heat tube inspection cable 1 according to an embodiment of the present invention. FIG. 2 is a perspective diagram illustrating the two segment units of the heat tube inspection cable 1 of FIG. 1. FIG. 3 is a perspective diagram illustrating insides of the segment units of the heat tube inspection cable 1 of FIG. 1. FIGS. 4A and 4B are for sectional diagram of the heat tube inspection cable 1 of FIG. 1.

Referring to FIGS. 1 through 4B, the heat tube inspection cable 1 according to the present embodiment includes a sensor unit 2 and a cable 3.

The sensor unit 2 detects a defect while moving within a heat tube. The sensor unit 2 is connected to a leading end of the cable 3. An eddy current test (ECT) probe sensor or an ultrasonic sensor may be employed for the sensor unit 2.

The cable 3 includes a first segment unit 10 connected to the sensor unit 2, a second segment unit 20 connected in the state of being rotated by a predetermined angle in a circumferential direction with respect to the first segment unit 10, a signal cable 30 to transmit electric signal from collected by the sensor unit 2, and a steel wire 40 to keep the linear configuration of the plurality of segment units like a bead necklace and to provide axial and bending strength.

The cable 3 may be structured by linking a plurality of segment units. The steel wire 40 may pass through the plurality of segment units. That is, the plurality of segment units may be threaded by the steel wire 40. For example, an outer coat of the cable 3 may include short cladding tubes of about 10 mm, made of engineering plastic.

While only two segment units, the first segment unit 10 and the second segment unit 20, are shown in FIGS. 2 and 3, the entire heat tube inspection cable 1 includes a plurality of segment units. The first segment unit 10 includes a body part 11, and a wheel part 12 contacting an inner circumference of the heat tube. The body part 11 may have a cylindrical shape with a diameter slightly smaller than an inner diameter of the heat tube. The body part 11 forms an exterior of the segment units.

A length of the body part 11 is determined corresponding to a radius of curvature of the heat tube. In further detail, the body part 11 may be manufactured relatively short when the curvature radius of the heat tube is small, and relatively long when the curvature radius is large. A wire through hole 115 for passage of the steel wire 40 may be formed through a center of the body part 11. The wire through hole 115 may linearly extend in a length direction of the body part 11.

A cable insertion part 111 for insertion of the signal cable 30 is formed on an outer circumference of the body part 11. The cable insertion part 111 may be helically formed on the outer circumference of the body part 11.

That is, the cable insertion part 111 may wind along the length of the body part 11. Although the present embodiment illustrates the cable insertion part 111 formed on the outer circumference of the body part 1, the cable insertion part 111 may be bored through an inside of the body part 11.

Therefore, the signal cable 30 is helically connected to the body part 11. Accordingly, concentration of tension on a portion of the signal cable 30 and concentration of a compressive force on another portion may be prevented while the heat tube inspection cable 1 is advancing in the heat tube. In other words, when the signal cable 30 extends helically rather than straightly, force is uniformly applied to the overall portion of the signal cable 30.

The cable insertion part 111 may be caved in by a predetermined depth to receive the signal cable 30 therein. For example, the cable insertion part 111 may be caved in by approximately a diameter of the signal cable 30 or more so that the signal cable 30 inserted in the cable insertion part 111 does not protrude out of the body part 11.

The body part 11 includes wheel insertion recesses 112 and 113 for insertion of the wheel part 12. The wheel insertion recesses 112 and 113 are caved in by a predetermined depth from the outer circumference of the body part 11. The wheel insertion recesses 112 and 113 include a first wheel insertion recess 112 disposed adjacent to a front end of the body part 11, and a second wheel insertion recess 113 disposed adjacent to a rear end of the body part 11. The first and the second wheel insertion recesses 112 and 113 are separated from each other by a predetermined interval in a length direction of the body part 11.

A plurality of the wheel insertion recesses 112 and 113 may be provided and arranged on the outer circumference of the body part 11 at a predetermined angular interval. For example, respectively three wheel insertion recesses may be formed on the outer circumference of the body part 11 at an interval of about 120°.

The first wheel insertion recess 112 and the second wheel insertion recess 113 may not be linear with each other.

That is, the second wheel insertion recess 113 may be disposed in a position rotated by a predetermined angle from the first wheel insertion recess 112, so as to prevent contact between the body part 11 and the inner circumference of the heat tube. For example, the wheel insertion recesses 112 and 113 may be disposed between respective neighboring cable insertion parts 111. Since the cable insertion parts 111 are helically formed on the body part 11, the second wheel insertion recess 113 can be disposed in the position rotated by the predetermined angle for the first wheel insertion recess 112.

The wheel insertion recesses 112 and 113 each include a rotation shaft 114 passing through the wheel part 12. The rotation shaft 114 supplies a center of rotation of the wheel part 112.

A plurality of the wheel parts 12 are connected to the body part 11. The wheel parts 12 may be rotatably connected to the body part 11 using the rotation shaft 114. The wheel parts 12 are received in the wheel insertion recesses 112 and 113. One side of each wheel part 12 protrudes out of the body part 11 while the other side is disposed in either of the wheel insertion recesses 112 and 113.

More specifically, one side of each wheel part 12 protrudes out of the body 11 and the other side is inserted to be proximate to the center of the body part 11.

Generally, friction force applied to the wheel part 12 is reversely proportional to a radius of the wheel part 12. Therefore, as described above, when one side of the wheel insertion recess 12 protrudes out of the body part 11 and the other side is inserted to be proximate to the center of the body part 11, the radius of the wheel part 12 may be maximized. As a consequence, friction applied to the wheel part 12 may considerably decrease.

The wheel part 12 includes a first wheel part 121 mounted to the first wheel insertion recess 112 and a second wheel part 122 mounted in the second wheel insertion recess 113.

A plurality of wheels constituting the first wheel part 121 and the second wheel part 122 are arranged at a predetermined interval on the outer circumference of the body part 11.

For example, each of the first wheel part 121 and the second wheel part 122 may be arranged at three positions at an angular interval of about 120° on the outer circumference of the body part 11.

The second wheel part 122 may be spaced apart from the first wheel part 121 by a predetermined interval. Since, as described above, the second wheel insertion recess 113 is at a position rotated by the predetermined angle from the first wheel insertion recess 112, the second wheel part 122 is disposed at a position rotated by the same angle from the first wheel part 121. Accordingly, the first wheel part 121 and the second wheel part 122 do not overlap when seen from a front of the body part 11. In other words, when seen from the front of the body part 11, the second wheel part 122 shows between respective two of the first wheel part 121.

For example, the first wheel part 121 and the second wheel part 122 may be arranged at about 120° interval on the outer circumference of the body part 11, respectively, while each of the second wheel part 122 is disposed between respective two first wheel part 121. When seen from the front of the body part 11, the wheel part 12 are arranged in such a manner that the first wheel part 121 and the second wheel part 122 are alternately arranged at an interval of about 60°, as shown in FIG. 4B.

A coat 13 covers an outside of the body part 11. The coat 13 prevents exposure and damage of the signal cable 30. The coat 13 includes holes 131 through which the wheel parts 12 protrude.

The signal cable 30 is connected with the body part 11 in a helically winding manner. Therefore, concentration of force on one certain portion of the signal cable 30 may be prevented. The signal cable 30 may be disposed between the respective wheels constituting the first wheel part 121 and the second wheel part 122.

The signal cable 30 is connected to not only the first and the second segment units 10 and 20 but also all the other segment units of the heat tube inspection cable 1.

The wire 40 passes through the body part 11, and more specifically, through the center of the body part 11.

The wire 40 passes through a plurality of the segment units constituting the heat tube inspection cable 1.

That is, all the segment units constituting the heat tube inspection cable 1 has a shape of bead necklace threaded with a wire. When the heat tube inspection cable 1 moves within the heat tube, the wire 40 is actually bent between the respective segment units. To bend the wire 40, a steel wire may be used as the wire 40 to supply bending flexibility to the heat tube inspection cable 1.

The second segment unit 20 has the same structure and the same shape as the first segment unit 10. That is, the second segment unit 20 includes a body part 21, and a wheel part 22 separated into a first wheel part 221 and a second wheel part 222. The body part 21 includes a cable insertion part 211 to insert the signal cable 30 therein.

The cable insertion part 211 of the second segment unit 20 helically winds around an outer circumference of the body part 21. Also, the cable insertion part 211 of the second segment unit 20 continues to the cable insertion part 111 of the first segment unit 10 considering that the signal cable 30 helically winds around both the first and the second segment units 10 and 20. Since the signal cable 30 is connected to all segment units constituting the heat tube inspection cable 1, cable insertion parts of all the segment units are successively connected.

The second segment unit 20 is connected in the state of being rotated by the predetermined angle with respect to the first segment unit 10. Accordingly, the wheel part 22 of the second segment unit 20 is arranged at the predetermined angle with respect to the wheel part 12 of the first segment unit 10, as opposed to being arranged linearly.

A connection tube 50 may be provided between the first segment unit 10 and the second segment unit 20 to protect the signal cable 30 exposed between the respective segment units. The connection tube 50 may be made of a flexible material to easily bend. An interval between the segment units constituting the heat tube inspection cable 1 may be adjusted by a length of the connection tube 50.

Hereinafter, the operation of the heat tube inspection cable 1 will be described.

Figure 5:
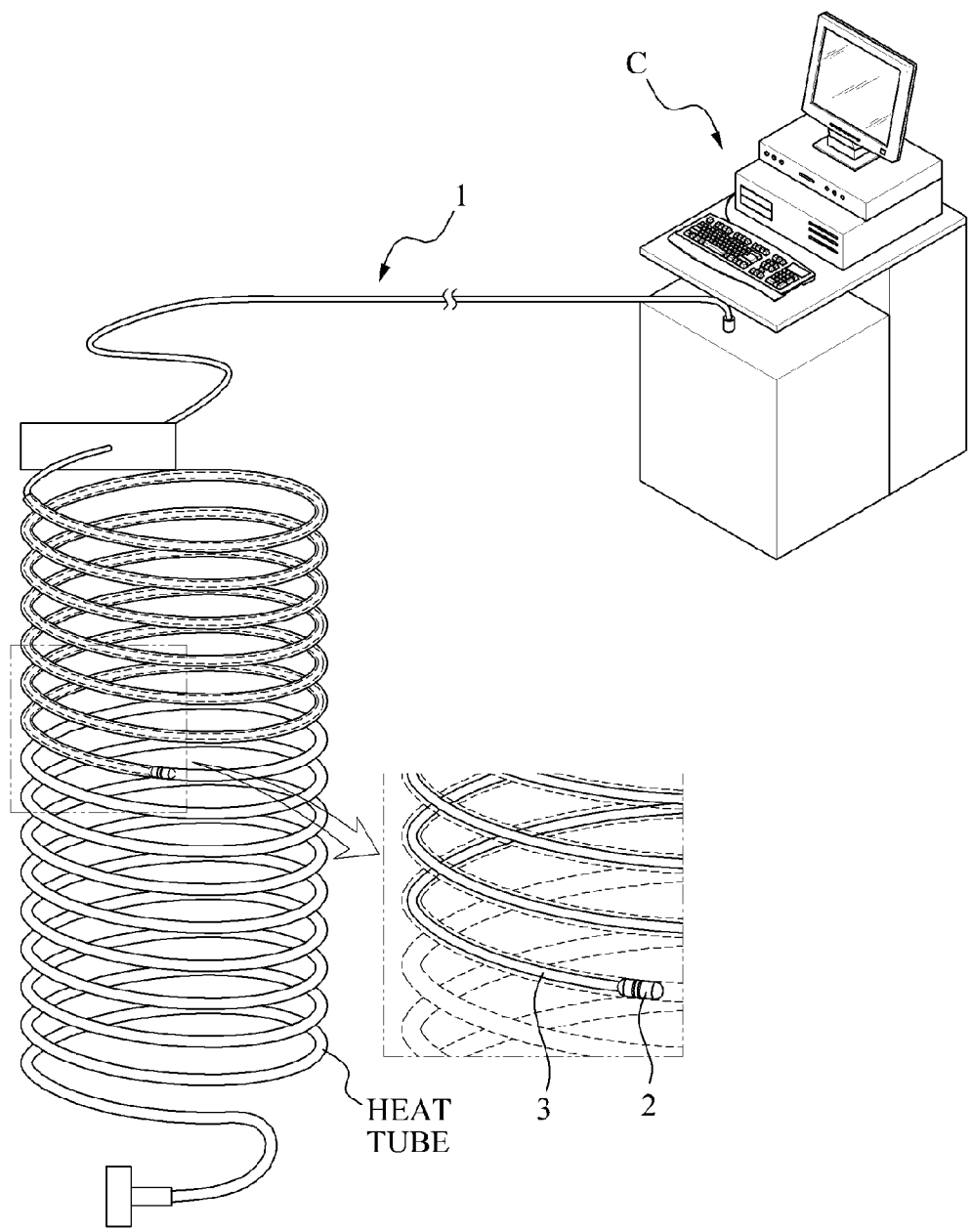
FIG. 5 is a schematic diagram illustrating the operation of the heat tube inspection cable of FIG. 1.

FIG. 5 is a schematic diagram illustrating the operation of the heat tube inspection cable of FIG. 2.

Referring to FIGS. 1 through 5, the heat tube inspection cable 1 is inserted in the heat tube, first, to inspect for defects in the heat tube. The heat tube inspection cable 1 may be inserted in the heat tube by an operator's pushing force.

The sensor unit 2 detects the defect in the heat tube in moving within the heat tube. The detection method is not specifically limited and may be any of generally known methods.

The wheel parts 12 contact the inner circumference of the heat tube, thereby reducing friction between the heat tube inspection cable 1 and the inner circumference of the heat tube. In addition, the heat tube inspection cable 1 may bend between the respective segment units in accordance with the curvature radius of the heat tube.

As the heat tube inspection cable 1 enters the heat tube, the force pushing the heat tube inspection cable 1 may be transmitted through the body part of each of the segment units. Therefore, the sensor unit 2 may advance up to the other end of the heat tube. When a defect in the heat tube is detected by the sensor unit 2, detection signal is sent to a computer C through the signal cable. The operator may check the signal on the defect through a monitor of the computer C.

The operator may pull the heat tube inspection cable 1 to withdraw the heat tube inspection cable 1 from the inside of the heat tube.

In the same manner as when the heat tube inspection cable 1 is inserted in the heat tube, friction between the heat tube inspection cable 1 and the inner circumference of the heat tube is reduced by the wheel part 12 and the heat tube inspection cable 1 may bend between the respective segment units.

However, different from when inserting the heat tube inspection cable 1 in the heat tube, the wire 40 is applied with tension when pulling the heat tube inspection cable 1.

Figure 6:
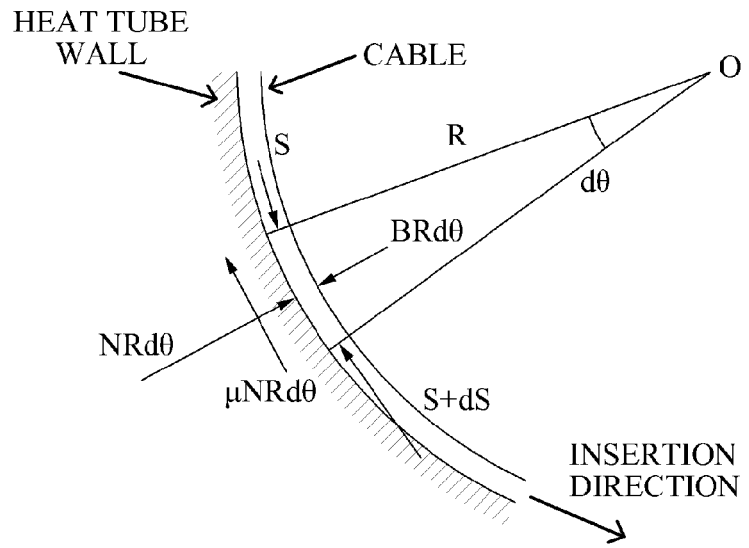
FIG. 6 is a schematic diagram illustrating force balance conditions between the heat tube inspection cable of FIG. 1 and the heat tube.
Figure 7:
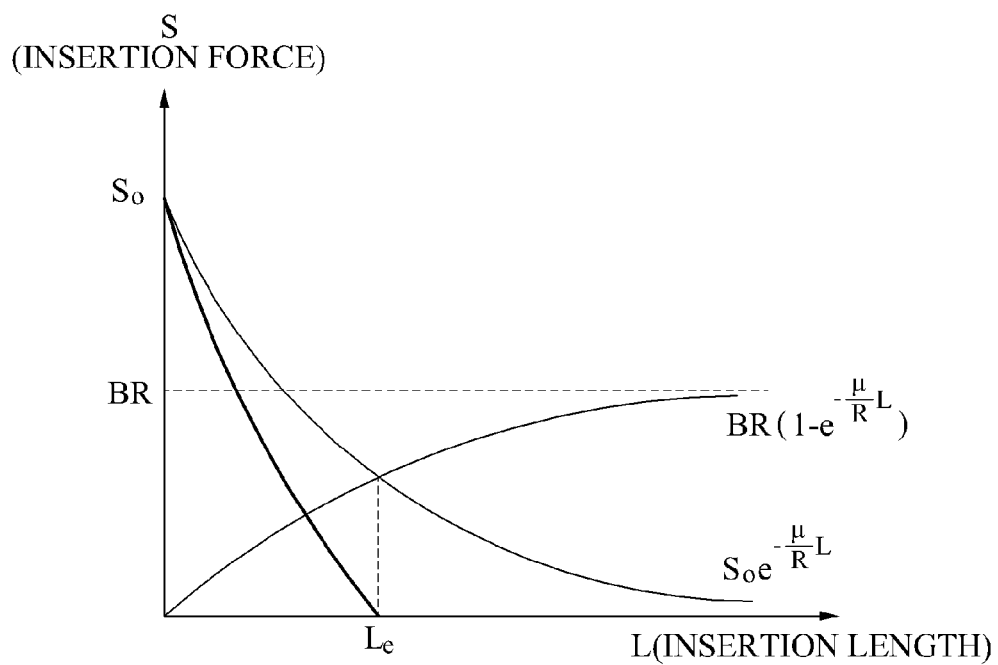
FIG. 7 is a graph illustrating an insertion force transmitted to the leading and of the cable corresponding to an insertion distance of the heat tube inspection cable of FIG. 1.

FIG. 6 is a schematic diagram illustrating force balance conditions between the heat tube inspection cable of FIG. 2 and the heat tube. FIG. 7 is a graph illustrating an insertion force transmitted corresponding to an insertion distance of the heat tube inspection cable of FIG. 2.

Referring to FIGS. 5 and 6, the heat tube is winding around a cylinder having a predetermined radius. However, for convenience of description, it may be presumed that the heat tube is a circular tube placed on a plane. In addition, conditions for inserting the cable 3 will be simply described as being under a condition where a flexible cable having a predetermined cross-section and bending stiffness is inserted in a circular tube without the sensor unit 2 disposed at the leading end of the cable 3.

The numerical analysis according to the present embodiment is performed on the following assumptions Assumption 1: The heat tube is a circular tube placed on a plane surface. That is, a helical angle is ignored.

Assumption 2: The cable 3 uniformly contacts an inner surface of the circular tube through the overall portion thereof.

Assumption 3: A contacting force by the bending stiffness of the cable 3 is uniform through the overall portion.

Assumption 4: A friction coefficient between the cable 3 and the circular tube is constant.

FIG. 6 shows conditions for balance of the forces considered when the cable 3 having flexibility and bending stiffness is inserted in the heat tube having a uniform curvature radius, that is, the circular tube. Parameters herein used include a curvature radius R of the circular tube, a cable insertion force S, an insertion position angle θ, a uniform contacting force B generated by the bending stiffness of the cable and other additional factors, a total vertical force N operated between the circular tube and the cable 3, and the friction coefficient μ between the circular tube and the cable 3.

Moment balance at the origin 0 may be calculated through Equation (1) below.

$$\Sigma H_O = RS - R(S+dS) - R(\mu NRd\theta) = 0 \qquad \text{Equation (1)}$$

The moment balance equation may be simplified to Equation (2) as below.

$$-dS = \mu NRd\theta \qquad \text{Equation (2)}$$

A force balance Equation (3) at a position where the circular tube and the cable contact is as follows.

$$\sum F_R = S\sin\frac{d\theta}{2} + (S+dS)\sin\frac{d\theta}{2} + BRd\theta - NRd\theta = 0 \qquad \text{Equation (3)}$$

The force balance equation may be simplified to Equation (4) as follows.

$$S + BR = NR \qquad \text{Equation (4)}$$

Equation (5) is obtained as follows by substituting equation (4) for Equation (2).

$$\frac{1}{S+BR}dS = -\mu d\theta \qquad \text{Equation (5)}$$

Equations (6) and (7) are obtained by performing integral calculus from an insertion starting position to a specific position angle as shown below. Here, the insertion position angle θ is zero in the insertion starting position and an insertion force at an entrance is $S_O$.

$$S_{S_O}^S \frac{1}{S+BR} = -S_0^\theta \mu d\theta \quad \text{Equation (6)}$$

$$\ln \frac{S+BR}{S_O+BR} = -\mu\theta \quad \text{Equation (7)}$$

The insertion force $S(\theta)$ transmitted to the insertion position angle θ is calculated by rearranging Equation (7) into Equation (8) as follows.

$$S(\theta)S_O e^{-\mu\theta} - BR(1-e^{-\mu\theta}) \quad \text{Equation (8)}$$

Equation (8) may be expressed with a number of rotation for insertion 'n' as follows.

$$\theta = 2\pi n \quad \text{Equation (9)}$$

$$S(\theta) = S_O e^{-\mu\theta} - BR(1-e^{-\mu\theta}) \quad \text{Equation (10)}$$

Also, Equation (12) may be obtained from Equation (8), as below, by using a relational Equation (11) regarding the insertion position angle θ and the insertion length L.

$$L = R\theta \quad \text{Equation (11)}$$

$$S(L) = S_O e^{-\frac{\mu}{R}L} - BR\left(1 - e^{-\frac{\mu}{R}L}\right) \quad \text{Equation (12)}$$

FIG. 7 is a graph illustrating the insertion force of Equation (12) by a function of the insertion length. In FIG. 7, $L_e$ refers to a maximum insertion length at which the insertion force is no longer transmitted.

The maximum insertion length where S=0 is calculated by Equation (13) below obtained from Equation (7) and Equation (11).

$$L_e = \frac{R}{\mu} \ln\left(1 + \frac{S_O}{BR}\right) \quad \text{Equation (13)}$$

Equation (13) shows that the maximum insertion length is inverse proportional to the friction coefficient. Accordingly, in a state where the same initial insertion force is applied to the same-diameter circular tube, when the friction coefficient μ reduces by half, the maximum insertion length may be doubled. The curvature radius of the circular tube is also a significant factor influencing the insertion efficiency.

An entrance insertion force $S_o$ necessary may be described as a function of the insertion length, Equation (14).

$$S_O = S_{tip} e^{\frac{\mu}{R}L} + BR\left(e^{\frac{\mu}{R}L} - 1\right) \quad \text{Equation (14)}$$

Equation (14) may be expressed in another manner as follows.

$$S_O(L) = (S_{tip} + BR)e^{\frac{\mu}{R}L} - BR \quad \text{Equation (15)}$$

In Equation (15), $S_{tip}$ refers to a minimum insertion force required for insertion of the sensor unit 2 attached to the leading end of the cable 3. Referring to Equation (14) and Equation (15), the entrance insertion force applied at the entrance of the tube to insert the cable 3 in the tube increases exponentially as the insertion length increases. Here, an increasing rate of the entrance insertion force increases as the friction coefficient increases.

To summarize, the insertion efficiency of the cable 3 is influenced by the friction coefficient, the curvature radius, and the bending stiffness of the cable 3. To be specific, the insertion efficiency of the cable 3 increases as the friction coefficient is low, the curvature radius is large, and the bending stiffness is small. Since the curvature radius of the tube is not a design parameter for the cable 3, the friction coefficient and the bending stiffness may be minimized to increase the insertion efficiency of the cable 3.

According to the equation for calculating the insertion force of the cable 3, a material having a low friction coefficient for the cable 3 may be used or a structure in a shape causing less friction, such as a wheel, may be adopted. In further detail, a Teflon cable, which has a relatively low friction coefficient, rather than a conventional Nylon-6 as the material of the cable 3 may be used. Also, when the wheel is used, a diameter of the wheel may be maximized.

Hereinafter, another embodiment of the present invention will be described. Since the present embodiment is distinctive from the previous embodiment in terms of the configuration of the wheel part, the signal cable, and the steel wire, only the distinctive features will be explained while citing the same features from the previous embodiment.

Figure 8:
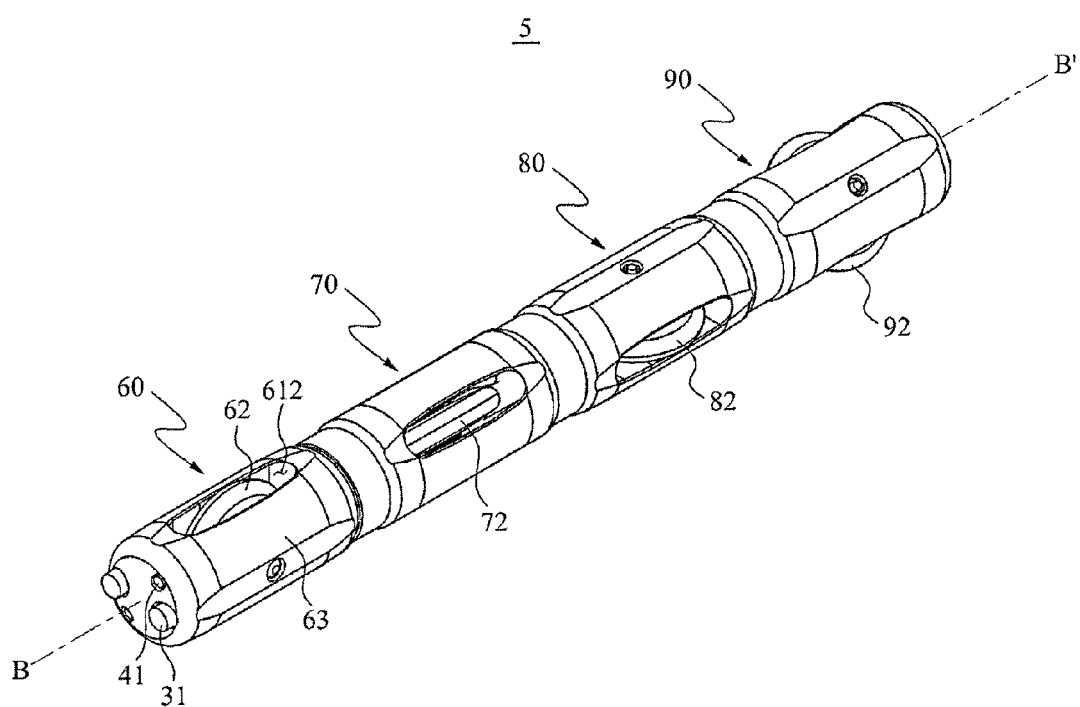
FIG. 8 is a perspective diagram illustrating four segment units of a heat tube inspection cable according to another embodiment of the present invention.
Figure 9A:
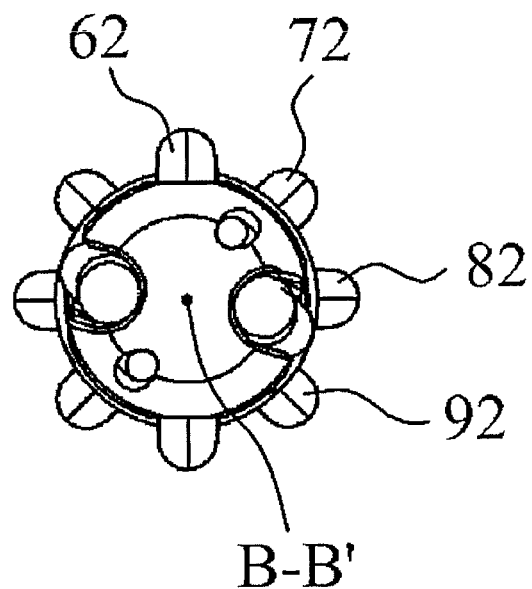
FIG. 9 is a perspective diagram illustrating an inside of the segment units of FIG. 8.
Figure 10A:
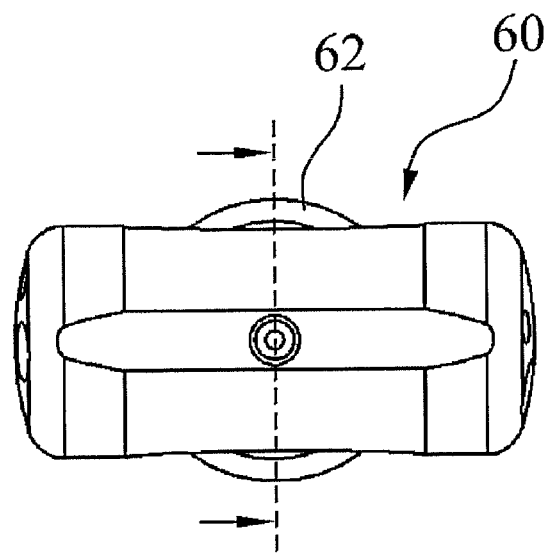
FIGS. 10A and 10B are for sectional diagram of the segment units of FIG. 8.
Figure 10B:
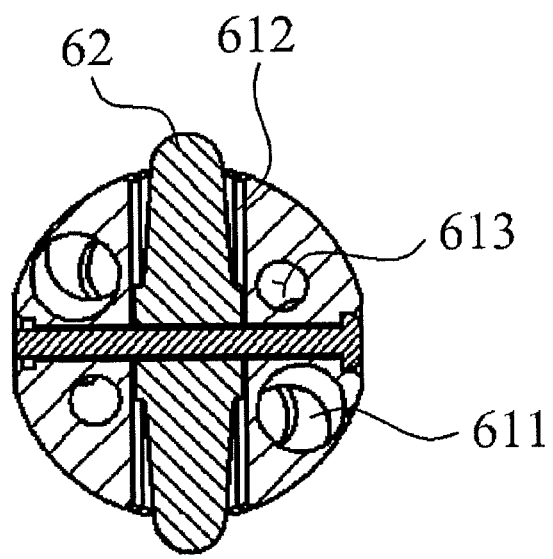

FIG. 8 is a perspective diagram illustrating a portion of a heat tube inspection cable according to another embodiment of the present invention. FIG. 9 is a perspective diagram illustrating an inside of the heat tube inspection cable of FIG. 8, and FIGS. 10A and 10B are sectional diagrams of the heat tube inspection cable of FIG. 8.

Referring to FIGS. 8 through 10B, a heat tube inspection cable 5 according to the present embodiment includes a first segment unit 60, a second segment unit 70 connected in a state of being rotated by a predetermined angle from the first segment unit 60, a third segment unit 80 connected in a state of being rotated by a predetermined angle from the second segment unit 70, a fourth segment unit 90 connected in a state of being rotated by a predetermined angle from the third segment unit 80, a signal cable 31 to transmit signal from by the sensor unit 2, and a wire 41 to keep the linear configuration of the plurality of segment units like a bead necklace and to provide axial and bending strength.

The first segment unit 60 includes a body part 61, and a wheel part 62 contacting an inner circumference of the heat tube.

The body part 61 includes a cable insertion part 611 to insert the signal cable 31 therein, a wheel hole 612 to pass the wheel part 62 therethrough, and a wire hole 613 to pass the wire 41 therethrough.

The cable insertion part 611 may be helically formed along an outer circumference of the body part 61. The cable insertion part 611 may wind along the length of the body part 61. According to this embodiment, a pair of the cable insertion parts 611 is helically formed on the body part 61.

In the same manner as in the previous embodiment, the cable insertion parts of the plurality of segment units constituting the heat tube inspection cable 5 helically and successively extend. For example, FIG. 9B shows cable insertion parts 611, 711, 811, and 911 of the first segment unit 60 to the fourth segment unit 90 which are helically and successively extending. In addition, the cable insertion part 611 may be symmetrically arranged with respect to a center line of body part 61. Accordingly, a force applied to the signal cable 31 may be distributed while the heat tube inspection cable 5 is moving in the heat tube.

The cable insertion part 611 is configured not to overlap the wheel hole 612 so as to prevent interference between the wheel part 62 and the signal cable 31.

The wheel hole 612 is formed cross through the body 61. The wheel hole 612 is formed slightly larger than the wheel part 62 so as not to interfere with the wheel part 62. The wheel hole 612 may have a slim shape corresponding to the wheel part 62. The wheel hole 612 may be disposed to pass a center of the body part 61 so that balance is maintained when the heat tube inspection cable 5 moves in the heat tube.

Since the respective segment units of the heat tube inspection cable 5 are in positions rotated from neighboring segment units, wheel holes of the segment units are accordingly in positions rotated from neighboring wheel holes. For example, in FIG. 9B, the first to the fourth segment units are rotated by about 45° from the neighboring segment units thereof.

The wheel part 62 is rotatably connected to the body part 61. The wheel part 62 protrudes to both sides of the body part 61 through the wheel holes 612. For this, a diameter of the wheel part 62 needs to be larger than a width of the body part 61.

Since the wheel holes of the respective segment units of the heat tube inspection cable 5 are rotated by a predetermined angle from the neighboring wheel holes thereof, wheel parts 62, 72, 82, and 92 of the segment units are accordingly rotated by the predetermined angle from neighboring wheel parts thereof. Accordingly, when seen from the front of the body part 61, the wheel parts of neighboring segment units do not overlap. For example, FIG. 9A shows that the wheel parts of the respective segment units of the heat tube inspection cable 5 are arranged at about 45° from the neighboring wheel parts without overlapping one another. Such an arrangement is to prevent contact between the body parts constituting the heat tube inspection cable 5 and the inner circumference of the heat tube.

The signal cable 31 helically winds around the body parts of the segment units while avoiding interference with the wheel part of the segment unit. A pair of the signal cables 31 may be provided. The pair of signal cables 31 may pass both sides of the wheel parts of the segment units.

The wire hole 613 may be bored to pass through both sides of the wheel part 62. Accordingly, the wire 41 may be symmetrically arranged with respect to the center line of body part of the respective segment units. As a result, the force applied to the wire 41 may be distributed while the heat tube inspection cable 5 is moving in the heat tube.

According to the present embodiment, friction between the wheel parts and the heat tube may be significantly reduced by greatly increasing a radius of each of the wheel parts in comparison to in the previous embodiment. Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A heat tube inspection cable comprising:
    a sensor unit configured to detect a defect in a heat tube;
    a plurality of segment units each configured to comprise a body part and a wheel part rotatably connected to the body part, wherein the body part of each of the plurality of segment units comprises:
        a cable insertion part helically formed on an outer circumference of the body part of each of the plurality of segment units, and
        a wire through hole formed through an inner part of the body part of each of the plurality of segment units;
    a signal cable configured to be inserted in the cable insertion parts and to helically pass through the body part of each of the plurality of segment units to transmit electric signal from the sensor unit; and
    a wire configured to be inserted in the wire through holes and to pass through the body part of each of the plurality of segment units to keep the linear configuration of the plurality of segment units like a bead necklace and to provide axial and bending strength.

2. The heat tube inspection cable of claim 1, wherein the cable insertion part of each of the plurality of segment units continues to a neighboring cable insertion part of a neighboring segment unit.

3. The heat tube inspection cable of claim 1, wherein a length of the body part of each of the plurality of segment units is adjusted corresponding to a radius of curvature of the heat tube.

4. The heat tube inspection cable of claim 1, wherein at least one of the wheel parts comprises a first wheel part, and a second wheel part spaced apart from the first wheel part by a predetermined interval, and
    the second wheel part is in a position rotated by a predetermined angle from the first wheel part.

5. The heat tube inspection cable of claim 1, wherein at least one of the wheel parts is disposed between respective neighboring cable insertion parts.

6. The heat tube inspection cable of claim 1, wherein one side of at least one of the wheel parts protrudes out of the body part while the other side extends to be proximate to an inner center of the body part.

7. The heat tube inspection cable of claim 1, wherein the signal cable is disposed among the plurality of wheel parts.

8. The heat tube inspection cable of claim 1, wherein at least one of the wheel parts is connected through the body part and both ends of the at least one of the wheel parts protrude out of the body part.

9. The heat tube inspection cable of claim 8, wherein at least one of the wheel parts comprises a single wheel, and a center of the single wheel is disposed in a center of the body part.

10. The heat tube inspection cable of claim 9, wherein the cable insertion part is symmetrically arranged with respect to a center line of the body part.

11. The heat tube inspection cable of claim 9, wherein the wire is symmetrically arranged with respect to the center line of the body part of each of the plurality of segment units.

12. The heat tube inspection cable of claim 1, wherein each of the plurality of segment units is connected in a state of being rotated by a predetermined angle from a neighboring segment unit.

13. A heat tube inspection cable comprising:
    a sensor unit configured to detect an inner circumference of a heat tube;
    a plurality of segment units each configured to comprise a body part and a wheel part, one side of at least one of the wheel parts protruding out of the body part and the other side extending to be proximate to an inner center of the body part; wherein the body part of each of the plurality of segment units comprises:
        a cable insertion part helically formed on an outer circumference of the body part of each of the plurality of segment units, and a wire through hole formed through an inner part of the body part of each of the plurality of segment units;

signal cables configured to be inserted in the cable insertion parts and to helically pass between the wheel parts of each of the segment units, and to extend in a length direction of the body part; and a wire configured to be inserted in the wire through holes and to pass through the body part of each of the segment units to keep the linear configuration of the plurality of segment units like a bead necklace and to provide axial and bending strength.

14. The heat tube inspection cable of claim 13, wherein each of the plurality of segment units is connected in a state of being rotated by a predetermined angle from a neighboring segment unit.

15. A heat tube inspection cable comprising:

a sensor unit configured to detect an inner circumference of a heat tube;

a plurality of segment units each configured to comprise a body part and a single wheel part passing through the body part, wherein the body part of each of the plurality of segment units comprises:

a cable insertion part helically formed on an outer circumference of the body part of each of the plurality of segment units, and a wire through hole formed through an inner part of the body part of each of the plurality of segment units;

a signal cable configured to be inserted in the cable insertion parts and to helically rotate at both sides of the single wheel part of each of the segment units, and to extend in a length direction of the body part; and a wire configured to be inserted in the wire through holes and to pass through the body part of each of the segment units to keep the linear configuration of the plurality of segment units like a bead necklace and to provide axial and bending strength, wherein both ends of each wheel part protrude out of each body part.

16. The heat tube inspection cable of claim 15, wherein each of the plurality of segment units is connected in a state of being rotated by a predetermined angle from their neighboring segment unit.

* * * * *